United States Patent [19]

Salesky

[11] Patent Number: 5,049,069

[45] Date of Patent: Sep. 17, 1991

[54] DIGITAL APICAL FORAMEN LOCATING APPARATUS WITH LINEAR GRAPHIC DISPLAY

[75] Inventor: Ronald D. Salesky, Tabernacle, N.J.

[73] Assignees: Leonard Salesky, Riverside; Phyllis S. Farber, Cherry Hill, both of N.J.

[21] Appl. No.: 481,088

[22] Filed: Feb. 16, 1990

[51] Int. Cl.⁵ .............................................. A61C 19/04
[52] U.S. Cl. ..................................... 433/27; 128/776; 128/777
[58] Field of Search ......................... 28/774, 776, 777; 433/72, 27

[56] References Cited

U.S. PATENT DOCUMENTS 4,353,693  10/1982  Dery et al. .......................... 433/27
4,526,179  7/1985  Salesky ............................... 128/776

FOREIGN PATENT DOCUMENTS 58-43028  3/1983  Japan ................................... 433/72

Primary Examiner—Lee S. Cohen
Assistant Examiner—Kevin Pontius
Attorney, Agent, or Firm—Norman E. Lehrer

[57] ABSTRACT

The digital apical foramen locating apparatus of the present invention utilizes the recognized fact that the conductance from the apical foramen to a patient's lip is not only equal to the conductance from the sulcus to the lip but is also constant from patient to patient. It further utilizes the recognition that there is a linear correspondence in the change of the conductance as the apical foramen is approached in root canal therapy. Utilizing this knowledge, the present invention employs a pair of fixed resistors to calibrate a single oscillator. This same oscillator is then used in the actual measurement and a comparison is made between the measured values and the stored reference values. In addition to a digital readout in 0.1 mm increments, there is an audible display whose cadence increases as the apex is approached and a graphical display which graphically illustrates to the dentist the location of the reamer in the canal and also the status of the probe's reliability.

9 Claims, 2 Drawing Sheets

DIGITAL APICAL FORAMEN LOCATING APPARATUS WITH LINEAR GRAPHIC DISPLAY

BACKGROUND OF THE INVENTION

The present invention is directed toward an instrument for locating the apical foramen in the tooth of a dental patient and, more particularly, toward such a device which measures and displays the distance from a point within the root canal of a tooth to the apex and which then accurately displays that distance both visually and audibly.

The apical foramen or apex is that anatomical point where the nerves enter a tooth. The passageway that these nerves follow once in the tooth is known as the root canal. When a tooth dies, there are two options: extraction or root canal therapy. Root canal therapy is a procedure wherein all of the dead tissue known as the pulp is removed from the tooth, leaving the bone which is functional for chewing even though the tooth is dead.

The location of the apical foramen is important to the root canal therapy procedure because the success of it depends on fully removing all dead tissue while not going past the apex which could cause an abscess by pushing the dead tissue into the tissue of the jaw. Originally, this point was located by successive X-rays. That is, an instrument was advanced into the canal a small amount, an X-ray was taken to find the location and this procedure was repeated until completed. It was well recognized, however, that this X-ray technique was inadequate and undesirable in that it resulted in too much exposure to X-rays and as a result of the fact that the nerve very often does not exit at the tip of the root. Depending on the angle of the X-ray, the reamer may, in fact, be very far past the apex when it appears to be at the tip of the root.

In the early 1960's, electronic devices were proposed for locating the apex by measuring the electrical resistance between an anode inserted into the canal and a cathode placed on a part of the human body such as the buccal mucous membrane.

It was empirically found that the conductance from the apical foramen to the lip was the same as the conductance from the gum line at the tooth (a point known as the sulcus) to the lip. Therefore, by measuring the conductance from the sulcus to the lip prior to root canal therapy, and looking for that same conductance measurement from the metallic reamer to the lip during the root canal procedure, one could electronically locate the apical foramen.

Prior U.S. Pat. No. 4,526,179 more specifically describes the history of electronic apical foramen locating apparatuses and discusses the deficiencies of each of the mentioned prior art devices. Rather than repeat that discussion at length, the text of that former patent is incorporated herein by reference.

The device shown in U.S. Pat. No. 4,526,179 was intended to overcome the deficiencies of the prior art discussed therein and provided a digital apical foramen locating apparatus which utilized the known equality in the conductances from the apex to the lip and from the lip to the sulcus as discussed above to numerically display the distance from a reamer to the apex. While this device has met with much success, it has been found that the numerical display does not adequately satisfy all doctors utilizing the device. Furthermore, this prior device, although calibrated at the factory, has been known to be subject to some drift due to aging of the components and ambient conditions.

SUMMARY OF THE INVENTION

The present invention is designed to overcome all of the disadvantages of the prior art devices known to the applicant and to provide a digital apical foramen locating apparatus which is substantially more accurate and which is substantially easier to use. Further clinical investigation has shown that the conductance measurement from the apical foramen to the patient's lip which is equal to the conductance from the lip to the sulcus is essentially constant from patient to patient. It has also been determined that there is a linear correspondence in the change of the conductance as the apical foramen is approached in root canal therapy. This linear region is from approximately 1.5 mm short of the apex to approximately 1.0 mm long of the apex. Utilizing this knowledge, the present invention utilizes a pair of fixed resistors to calibrate a single oscillator. This same oscillator is then used in the actual measurement and a comparison is made between the measured values and the stored reference values. In addition to a digital readout in 0.1 mm increments, there is a graphical display which graphically illustrates to the dentist the location of the reamer in the canal and also the status of the probe's reliability, i.e. whether it is short or open circuited.

BRIEF DESCRIPTION OF THE DRAWING

For the purpose of illustrating the invention, there is shown in the accompanying drawing one form which is presently preferred; it being understood that the invention is not intended to be limited to the precise arrangements and instrumentalities shown.

DETAILED DESCRIPTION OF THE PREFERRED EMBODIMENT

Figure 1:
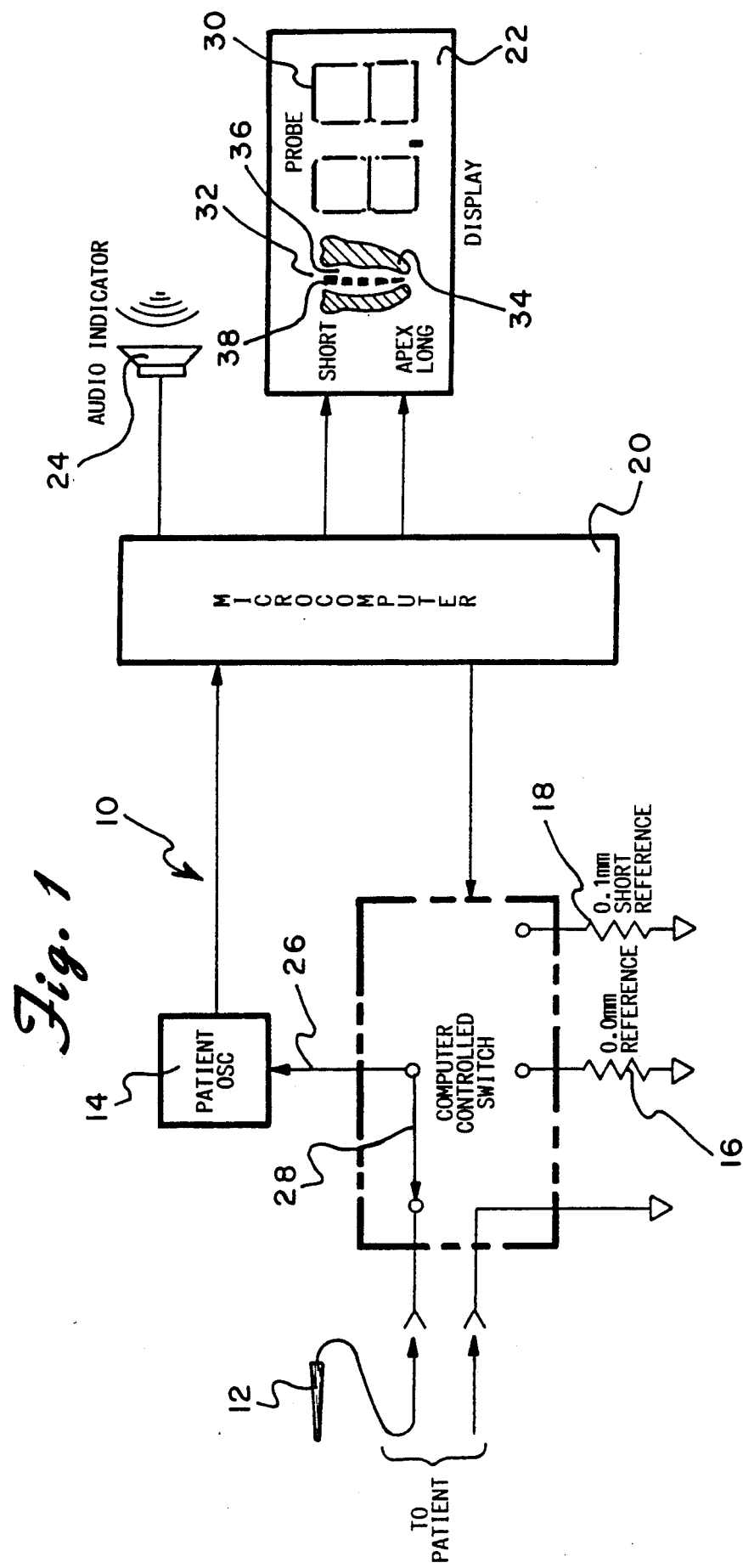
FIG. 1 is a schematic block diagram of the digital apical foramen locating apparatus constructed in accordance with the principles of the present invention.

Referring now to the drawings in detail, there is shown in FIG. 1 a schematic block diagram of a digital apical foramen locating apparatus constructed in accordance with the principles of the present invention and designated generally as 10. The system 10 is comprised essentially of six major components: a probe in the form of a reamer 12, an oscillator 14, a pair of reference resistors 16 and 18, a microcomputer 20, a digital and graphical display 22 and an audio indicator 24.

Probe 12 is a standard well-known probe in the form of a reamer. As is known in the art, the tip of the reamer is inserted into the root canal and makes electrical contact with the tissue therein.

Oscillator 14 is also, per se, a well-known device. This oscillator has a frequency of operation which is affected by the conductance connected to its input 26. This is true, of course, only if the conductance is within a certain range. Through three-position switch 28, the input 26 of oscillator 14 can be connected to the probe 12. The frequency and, therefore, the corresponding period, of the oscillator 14 is then varied depending o the position of the probe.

Three-position switch 28 is also capable of being selectively connected to either resistor 16 or resistor 18. Through clinical investigations, it has been empirically determined that conductance is substantially constant from patient to patient and also that there is a linear correspondence in the change of conductance as the apical foramen is approached in root canal therapy. This linear region is approximately 1.5 mm short of the apex to 1.0 mm long of the apex. Resistor 16 represents the conductance at the apex, i.e. at 0.0 mm. The value of this resistor 16 that satisfies this condition is 4.02K. Resistor 18 is selected so as to correspond with the position of the probe at a distance of 0.1 mm short of the apex. The value of this resistor has empirically been found to be 4.22K.

Switch 28 may be a manually operated switch. Preferably, however, switch 28 is an electronically operated switch which is controlled by the microcomputer 20 in a manner which will be explained more fully hereinafter.

Microcomputer 20 performs several functions. As will be described more fully below, microcomputer 20 controls the taking of the reference measurements from resistors 16 and 18 and the taking of measurements from the oscillator 14 while connected to the patient through the probe 12. The microcomputer interprets these readings and generates output signals representing the same.

Digital and graphic display 22 which is connected to the output of the microcomputer 20 includes two distinct displays. Digital display 30 is of a conventional type and displays the distance computed by the microcomputer 20 in 0.1 mm increments. Graphic display 32 is a unique display in the shape of a tooth 34 having a canal 36. A graphic display in the form of a segmented reamer or line 38 appears in the canal 36. Each of the individual segments is turned on or off by the microcomputer 20 and represents a fixed distance such as 0.1 mm from the apex.

Audio indicator 24 is also connected to the output of the microcomputer 20 and gives a audible indication of the distance of the probe to the apex. This audible indication may be in the form of beeps or the like whose cadence increases as the apex is approached.

The system 10 takes its measurements and calculates the displays in the following manner. When the system is initiated, the oscillator 14 is connected to resistor 16 through switch 28 as controlled by the microcomputer 20. The period of the oscillator 14 is measured and is stored for later use. This particular period can be referred to as the null point reference.

The switch 28 then connects the oscillator 14 to resistor 18 which represents the conductance when the reamer is 0.1 mm short of the apex. The period of the oscillator is measured and this data which can be referred to as the tenth point reference is stored for later use.

The microcomputer 20 then calculates the oscillator period to depth ratio. This is the slope of the line that relate the oscillator period to the root canal depth and is calculated by the simple arithmetic calculation: slope=tenth point−null point.

With the device now calibrated, the oscillator 14 is then terminated with the probe 12 to the patient through the automatic control of switch 28. As the probe is being used by the dentist, the microcomputer 20 takes the period of the oscillator 14 and calculates the distance from the apex based on the slope and null point measurement. This calculation, performed by the microcomputer, is as follows: Distance from apex=(patient measurement period−null point)/slope.

The location of the probe or reamer relative to the apex is determined by the sign of the above calculation. If it is negative, the reamer is long of the apex, i.e. it has passed the same. If the calculation is non-zero, the reamer is short of the apex, i.e. still in the canal. If the calculation is zero, the reamer is at the apex.

The microcomputer 20 then displays this information in several manners. The numerical result is displayed in the digital portion 30 of the display 22. The relative location of the reamer, that is, whether it is short of the apex or past it may also be displayed by means of a simple enunciator built into the display.

In addition to the digital display 30 the position of the reamer, that is, the depth of the reamer into the canal, is also graphically displayed in the graphic display 32. The successive segments 38 are generated at preset distances from the apex. These may be set, for example, to be displayed at each millimeter or at each 0.1 mm or at some other preselected increment. Preferably this graphical display is generated by means of a lookup table stored in the computer 20 and the calculated distance from the apex as measured above. The calculated distance from the apex gives the lookup location to use to obtain the information on what segments should be displayed.

It has also been found that an audible sound is often helpful to a dentist when he is attempting to locate the apex. Thus, the audio indicator in the form of a speaker or the like 24 is provided which generates an audible signal in the form of a series of beeps or pulses or the like. The cadence of these audible pulses increases as the apex is approached. This cadence preferably increases with each 0.1 millimeter movement toward the apex. As with the graphic display 32, the audio indicator information is also generated by means of the same lookup table and the calculated distance from the apex. Again, the calculated distance gives the lookup location to use to obtain the information on what cadence should be given to the audio signal.

In order to ensure the quality of the probe and associated lead wires, etc., the microcomputer 20 includes a program for constantly checking the probe. Before the oscillator period is used to calculate a display, it is compared to the known limits of the oscillator range, i.e. with a short-circuited or open-circuited probe termination. If the oscillator period measurement indicates the probe is open or short circuited, that information is instead displayed for the user by an appropriate enunciator and/or audio signal.

Figure 2:
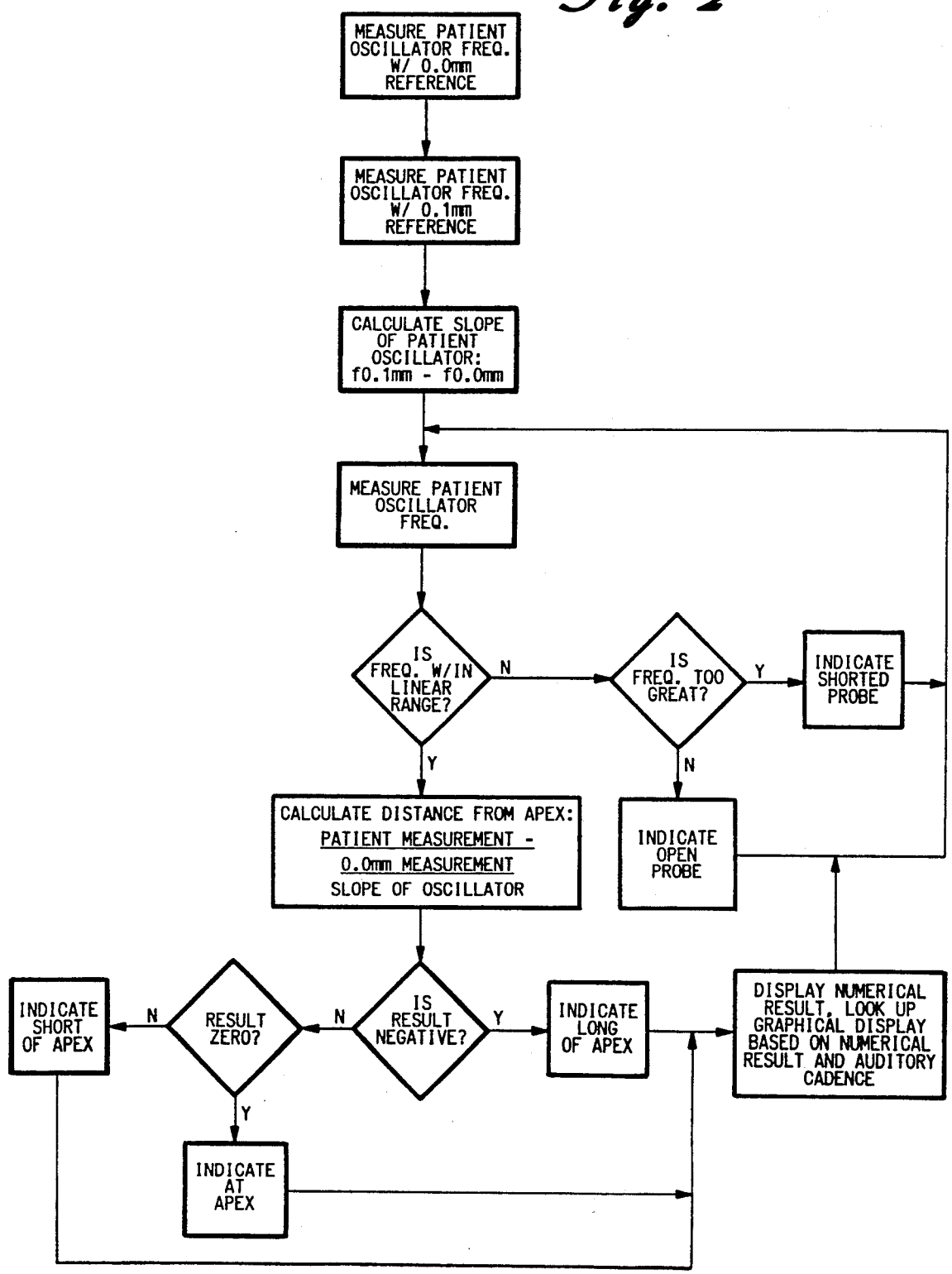
FIG. 2 is a functional flowchart explaining the operation of the system shown in FIG. 1.

FIG. 2 is a functional flowchart showing the manner in which the digital apical foramen locating apparatus 10 of FIG. 1 operates. This flowchart essentially summarizes the more detailed description disclosed hereinabove.

The present invention may be embodied in other specific forms without departing from the spirit or essential attributes thereof and accordingly reference should be made to the appended claims rather than to the foregoing specification as indicating the scope of the invention.

I claim:

1. In an apical foramen locating device including a probe intended to be inserted into the root canal of a tooth, an electrical circuit means connected to said probe for generating an output signal indicative of the distance between said probe in said canal and the apex and means connected to said electrical circuit means for producing a visual display representing said distance, the improvement in said display means wherein said display is in the form of a line and wherein means are provided for adjusting the length of said line depending on the distance of said probe to the apex.

2. The invention as claimed in claim 1 wherein said visual display means further includes the illustration of a tooth with an interior elongated canal therein and wherein said line is located within said elongated canal.

3. The invention as claimed in claim 2 wherein one end of said elongated canal represents the exterior of said root canal and wherein the other end represents the position of the apex and wherein said line can extend from the first-mentioned end of said elongated canal to a point adjacent the second-mentioned end thereof.

4. The invention as claimed in claim 3 wherein said line can extend entirely through said elongated canal and beyond the location of the apex.

5. The invention as claimed in claim 1 wherein said line is comprised of a plurality of segments and wherein each successive segment is displayed to form said line as said probe approaches the apex.

6. The invention as claimed in claim 5 wherein each segment of said line represents a predetermined fixed distance that said probe travels as it approaches the apex.

7. The invention as claimed in claim 1 further including means for numerically displaying the distance of said probe to the apex.

8. The invention as claimed in claim 1 further including means for generating an audible signal representing the distance of said probe to the apex.

9. The invention as claimed in claim 8 wherein said audible signal is in the form of a series of beeps and further including means for increasing the cadence of said beeps as the probe is moved closer to the apex.

* * * * *